US012266121B2

(12) United States Patent
Sakamoto et al.

(10) Patent No.: US 12,266,121 B2
(45) Date of Patent: Apr. 1, 2025

(54) MEDICAL IMAGE DATA CREATION APPARATUS FOR TRAINING, MEDICAL IMAGE DATA CREATION METHOD FOR TRAINING AND NON-TRANSITORY RECORDING MEDIUM IN WHICH PROGRAM IS RECORDED

(71) Applicant: OLYMPUS CORPORATION, Tokyo (JP)

(72) Inventors: Joji Sakamoto, Hachioji (JP); Akihiro Kubota, Kokubunji (JP); Yamato Kanda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 17/864,574

(22) Filed: Jul. 14, 2022

(65) Prior Publication Data

US 2022/0351396 A1 Nov. 3, 2022

Related U.S. Application Data

(63) Continuation of application No. PCT/JP2020/001783, filed on Jan. 20, 2020.

(51) Int. Cl.
*G06T 7/00* (2017.01)
*G06T 7/38* (2017.01)

(52) U.S. Cl.
CPC ...... *G06T 7/38* (2017.01); *G06T 2207/20081* (2013.01); *G06T 2207/30096* (2013.01)

(58) Field of Classification Search
CPC ............ G06T 7/38; G06T 2207/20081; G06T 2207/30096; G06T 2207/10016; G06T 2207/10068; G06T 2207/10152; G06T 7/0012; A61B 1/045
See application file for complete search history.

(56) References Cited

U.S. PATENT DOCUMENTS

| 2016/0133018 A1* | 5/2016 | Machado | G06T 3/18 |
| | | | 382/131 |
| 2016/0228075 A1* | 8/2016 | Kitamura | A61B 6/12 |
| 2018/0249889 A1* | 9/2018 | Imai | A61B 1/0655 |
| 2019/0235195 A1 | 8/2019 | Uemura | |
| 2021/0076917 A1* | 3/2021 | Kamon | A61B 1/0661 |

(Continued)

FOREIGN PATENT DOCUMENTS

| JP | 2005-185560 A | 7/2005 |
| JP | 6483890 B1 | 3/2019 |
| WO | 2019/235195 A1 | 12/2019 |

OTHER PUBLICATIONS

International Search Report dated Mar. 24, 2020 received in PCT/JP2020/001783.

*Primary Examiner* — Van D Huynh
(74) *Attorney, Agent, or Firm* — Scully, Scott, Murphy & Presser, P.C.

(57) ABSTRACT

A medical image data creation apparatus for training acquires a first medical image, acquires a second medical image that is different from the first medical image and is obtained by photographing a substantially same spot as in the first medical image, creates lesion region information concerning a lesion part in the second medical image, and creates medical image data for training in which the first medical image and the lesion region information are associated with each other.

10 Claims, 4 Drawing Sheets

(56) References Cited

U.S. PATENT DOCUMENTS

2021/0097331 A1\* 4/2021 Kamon .................. H04N 7/183
2021/0161363 A1\* 6/2021 Makino .................. G06N 3/084
2022/0130047 A1\* 4/2022 Saha .................... A61B 5/6821
2022/0207722 A1\* 6/2022 Kim .......................... G06T 7/11
2022/0335610 A1\* 10/2022 Shiratani ................ G06V 10/82

\* cited by examiner

MEDICAL IMAGE DATA CREATION APPARATUS FOR TRAINING, MEDICAL IMAGE DATA CREATION METHOD FOR TRAINING AND NON-TRANSITORY RECORDING MEDIUM IN WHICH PROGRAM IS RECORDED

CROSS REFERENCE TO RELATED APPLICATION

This application is a continuation application of PCT/JP2020/001783 filed on Jan. 20, 2020, the entire contents of which are incorporated herein by this reference.

BACKGROUND OF THE INVENTION

1. Field of the Invention

The present invention relates to a medical image data creation apparatus for training configured to create medical image data for training, a medical image data creation method for training, and a non-transitory recording medium in which a program is recorded.

2. Description of the Related Art

In recent years, a computer diagnosis support apparatus (CAD: computer-aided detection/diagnosis) has been developed, which shows a candidate position of a lesion part in a medical image (CADe: Computer-Aided Detection) and displays differential information by outputting quantitative data related to the candidate of the lesion part (CADx: Computer-Aided Diagnosis). For example, Japanese Patent Application Laid-Open Publication No. 2005-185560 proposes a medical image processing system configured to cause an apparatus to learn a medical image as training data, and detect or differentiate a lesion part. Japanese Patent Application Laid-Open Publication No. 2005-185560 discloses the medical image processing system that makes the training data updatable and enhances CAD expertise.

SUMMARY OF THE INVENTION

A medical image data creation apparatus for training of one aspect of the present invention includes at least one processor including hardware. The processor acquires a first medical image, acquires a second medical image that is different from the first medical image and is obtained by photographing a substantially same spot as in the first medical image, performs alignment of the first medical image and the second medical image, creates lesion region information concerning a lesion part in the second medical image, the alignment of which is performed, and creates medical image data for training in which the lesion region information in the second medical image, the alignment of which is performed, is associated with the first medical image.

A medical image data creation method for training of one aspect of the present invention includes: acquiring a first medical image; acquiring a second medical image that is different from the first medical image and is obtained by photographing a substantially same spot as in the first medical image; performing alignment of the first medical image and the second medical image; creating lesion region information concerning a lesion part in the second medical image, the alignment of which is performed; and creating medical image data for training in which the lesion region information in the second medical image, the alignment of which is performed, is associated with the first medical image.

A non-transitory recording medium of one aspect of the present invention records a program. The program causes a computer to execute: acquiring a first medical image; acquiring a second medical image that is different from the first medical image and is obtained by photographing a substantially same spot as in the first medical image; performing alignment of the first medical image and the second medical image; creating lesion region information concerning a lesion part in the second medical image, the alignment of which is performed; and creating medical image data for training in which the lesion region information in the second medical image, the alignment of which is performed, is associated with the first medical image.

DETAILED DESCRIPTION OF THE PREFERRED EMBODIMENTS

Hereinafter, an embodiment is described using the drawings.

(System Configuration)

Figure 1:
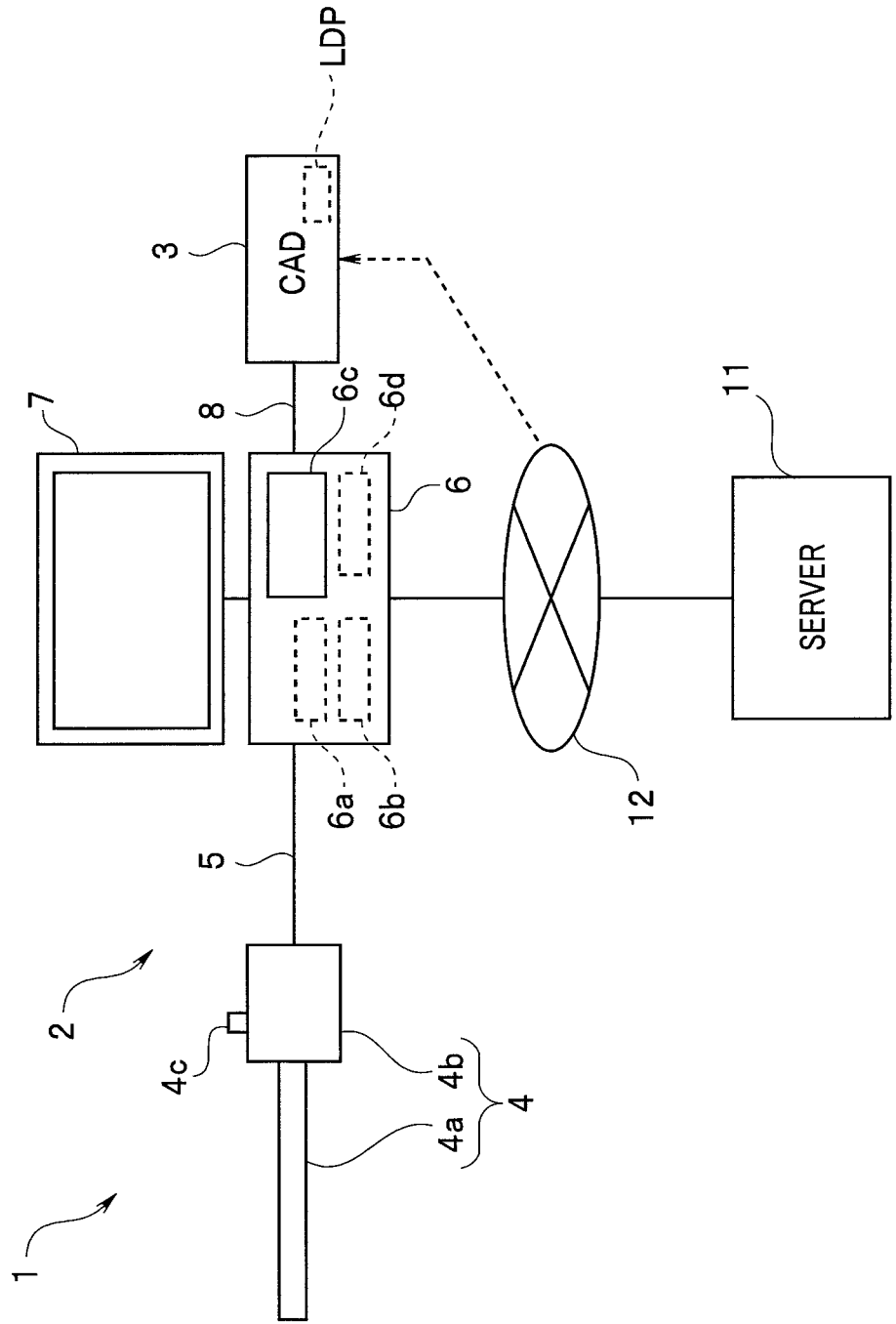
FIG. 1 is a configuration diagram of a medical system according to a present embodiment.

FIG. 1 is a configuration diagram of a medical system according to the present embodiment. The medical system 1 is an endoscope system, and includes an endoscope apparatus 2, and a computer diagnosis support apparatus (hereinafter, referred to as a CAD apparatus) 3. The endoscope apparatus 2 has an endoscope 4 having an insertion portion 4a, a video processor 6 to which a universal cable 5 extended from the endoscope 4 is connected, and a display apparatus 7 connected to the video processor 6. The endoscope apparatus 2 is connected to the CAD apparatus 3 by a signal line 8.

When a doctor inserts the insertion portion 4a into a subject, an image of a site of an inside of the subject that is obtained through an observation window at a distal end portion of the insertion portion 4a is displayed on the display apparatus 7 as an endoscope image. The doctor looks at the endoscope image displayed on the display apparatus 7, and performs detection and differentiation of a lesion part. Note that, from a distal end of the insertion portion 4a, as an illumination light with which an inspection site is illuminated, light from a light source apparatus 6d provided in the video processor 6 is emitted from an illumination window at the distal end portion of the insertion portion 4a through a lightguide that is inserted through an inside of the insertion portion 4a.

The video processor 6 has a control unit 6a, a storage apparatus 6b, an operation panel 6c, and the light source apparatus 6d. A doctor or the like can operate the operation panel 6c, and can give various instructions to the endoscope apparatus 2. The endoscope apparatus 2 has a first observation mode, and a second observation mode that is different from the first observation mode. The endoscope apparatus 2 has two observation modes that are a white light observation mode that is a so-called normal light observation mode, and a narrowband light observation mode that is a so-called special light observation mode. Switching of the observation mode can be performed by a doctor or the like operating the operation panel 6c. Accordingly, the doctor can select one desired observation mode from the two observation modes and can observe an inside of a subject. Note that the doctor can also switch the observation mode during observation.

The light source apparatus 6d emits white light when the observation mode is the white light observation mode, and emits predetermined narrowband light when the observation mode is the narrowband light observation mode. The white light is wideband light including RGB wavelengths. The narrowband light is two narrowband lights having center wavelengths of 415 nm and 540 nm, for example.

A reflection light from an observation site is photoelectrically converted by an image pickup device not illustrated and an endoscope image is generated. The generated endoscope image is displayed on the display apparatus 7, and can be stored in the storage apparatus 6b as a still image or a moving image by the doctor pressing down a release switch 4c provided at an operation portion 4b of the endoscope 4. Accordingly, image data of the endoscope images in a still image and a moving image that are obtained in the respective observation modes are recorded in the storage apparatus 6b.

The control unit 6a includes a central processing unit (CPU), a ROM, and a RAM. The storage apparatus 6b is a rewritable large-capacity nonvolatile memory such as a hard disk apparatus. The control unit 6a realizes various functions of the endoscope apparatus 2 by reading a software program for various functions that are stored in the ROM and the storage apparatus 6b, expanding the software program into the RAM and executing the software program.

The endoscope apparatus 2 and the CAD apparatus 3 are communicable by the signal line 8. Image data of the endoscope image from the endoscope apparatus 2 are inputted to the CAD apparatus 3 in real time. The CAD apparatus 3 detects a lesion part in the image data of the endoscope image that are inputted, and outputs detection result information of the lesion part to the endoscope apparatus 2. The endoscope apparatus 2 displays the detection result information with the endoscope image on the display apparatus 7.

The CAD apparatus 3 has a lesion part detection program LDP. Here, a lesion part detection algorithm of the lesion part detection program LDP uses a model obtained by performing machine learning with the image data including the lesion part as training data. Accordingly, the CAD apparatus 3 performs detection of a lesion part in the endoscope image received from the endoscope apparatus 2 in real time by using the lesion part detection program LDP. When finding the lesion part in the endoscope image, the CAD apparatus 3 extracts region information of the lesion part that is found, and transmits a detection message of the lesion part and the like to the endoscope apparatus 2. The detection message from the CAD apparatus 3 is displayed on the display apparatus 7 of the endoscope apparatus 2. As a result, the doctor can recognize a lesion part detection result from the CAD apparatus 3 while looking at the endoscope image displayed on the display apparatus 7.

The endoscope apparatus 2 is connected to a server 11 by a network 12. The network 12 may be the Internet, or a LAN. The server 11 has a processor 13 and a storage apparatus 14. As described later, the server 11 has a training data creation program TDC that creates training data from the image data of the endoscope image obtained in the endoscope apparatus 2.

Figure 2:
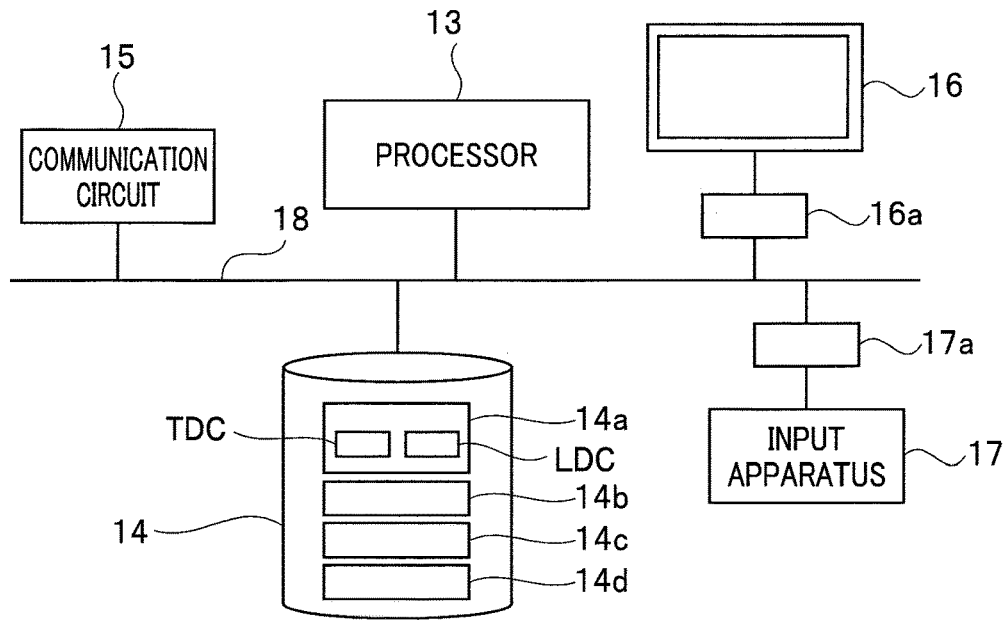
FIG. 2 is a block diagram showing a configuration of a server according to the present embodiment.

FIG. 2 is a block diagram showing a configuration of the server 11. The server 11 has the processor 13, the storage apparatus 14, a communication circuit 15, a display apparatus 16, and an input apparatus 17 including a keyboard and a mouse. The processor 13, the storage apparatus 14, the communication circuit 15, the display apparatus 16, and the input apparatus 17 are connected to one another via a bus 18. Note that the display apparatus 16 and the input apparatus 17 are connected to the bus 18 via interfaces (I/F) 16a and 17a respectively.

The processor 13 includes a central processing unit (CPU), a ROM, and a RAM. The processor 13 reads and executes programs stored in the ROM and the storage apparatus 14. Note that a part of the processor 13 may be configured by a semiconductor apparatus such as FPGA (field programmable gate array), an electronic circuit or the like.

The storage apparatus 14 includes a program storage region 14a configured to store various programs, a first image storage region 14b configured to store a first image G1, a second image storage region 14c configured to store a second image G2, and a training data storage region 14d configured to store training data. The first image G1 is a white light image obtained in the white light observation mode in the endoscope apparatus 2, and the second image G2 is a narrowband light image obtained in the narrowband light observation mode in the endoscope apparatus 2.

The program storage region 14a includes the training data creation program TDC and the lesion part detection algorithm creation program LDC. The training data creation program TDC is a software program configured to create training data for the lesion part detection algorithm by using the endoscope image obtained in the endoscope apparatus 2. A process of the training data creation program TDC is described later.

The lesion part detection algorithm of the lesion part detection algorithm creation program LDC is an algorithm trained by using training data created by the training data creation program TDC. The lesion part detection algorithm creation program LDC generates a program of a part corresponding to a detection algorithm of the lesion part detection program LDP that is stored in the CAD apparatus 3.

Note that here, the training data creation program TDC is executed in the server 11, but may be executed in a computer such as a personal computer.

(Creation Process of Training Data)

Figure 3:
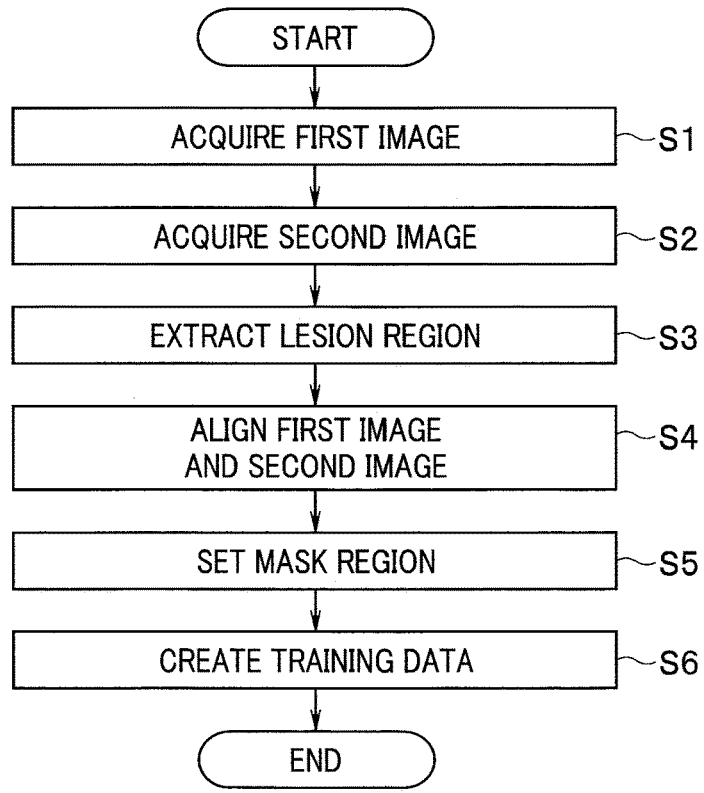
FIG. 3 is a flowchart showing an example of a flow of processing of image data according to the present embodiment.

A creation process of the training data is described. FIG. 3 is a flowchart showing an example of a flow of processing of image data. FIG. 3 shows a process of the training data creation program TDC. The training data creation program TDC is read from the storage apparatus 14 and is executed by the processor 13.

Before the creation process of the training data is performed, the endoscope images of the respective observation modes that are acquired in the endoscope apparatus 2 are transferred to the server 11 via the network 12. The white light images that are photographed in the white light observation mode and acquired are stored in the first image storage region 14b as the first image G1. The narrowband light images that are photographed in the narrowband light observation mode and acquired are stored in the second image storage region 14c as the second image G2. Accordingly, image data of many endoscope images in the two observation modes that are acquired at each inspection in the endoscope apparatus 2 are stored and accumulated in the first image storage region 14b and the second image storage region 14c.

Note that here, the image data of the first image G1 and the second image G2 are transferred to the server 11 from the endoscope apparatus 2 via the network 12. However, the image data of the first image G1 and the second image G2 may be transferred to a storage medium such as a USB (universal serial bus) memory from the storage apparatus 6b and recorded in the storage medium, the storage medium may be fitted to the server 11, and the image data of the first image G1 and the second image G2 may be stored in the first image storage region 14b and the second image storage region 14c.

The processor 13 executes the training data creation program TDC and creates the training data by using the first image and the second image. First, the processor 13 acquires the first image G1 from the first image storage region 14b (Step (hereinafter, abbreviated as S) 1). Acquisition of the first image G1 is performed by causing a data creator who creates the training data to select one image from a plurality of endoscope images stored in the first image storage region 14b. For example, the data creator causes the display apparatus 16 to display a plurality of white light images stored in the first image storage region 14b and selects, by the input apparatus 17, one white light image from the plurality of white light images that are displayed.

Next, the processor 13 acquires the second image G2 from the second image storage region 14c (S2). Acquisition of the second image G2 is also performed by causing the data creator who creates the training data to select one endoscope image from a plurality of endoscope images stored in the second image storage region 14c. For example, the data creator causes the display apparatus 16 to display a plurality of narrowband light images stored in the second image storage region 14c, and selects one narrowband light image from the plurality of narrowband light images that are displayed.

Accordingly, the process in S1 configures a first image acquisition unit configured to acquire a first medical image. A process in S2 configures a second image acquisition unit that acquires a second medical image that is different from the first medical image and is obtained by photographing a substantially same spot as in the first medical image.

Note that when the white light image stored in the first image storage region 14b is a moving image, the data creator temporarily stops the moving image while watching the moving image that is being reproduced, and one specified still image is selected and acquired as the first image G1. Similarly, when the narrowband light image stored in the second image storage region 14c is a moving image, the data creator temporarily stops the moving image while watching the moving image that is being reproduced, and one specified still image is selected and acquired as the second image G2. In other words, the first medical image and the second medical image may be still images that are respectively selected from moving images.

The processor 13 extracts a lesion region of a lesion part in the acquired second image G2 (S3). The lesion region of the lesion part can be extracted based on a difference in color tone in the second image G2, presence or absence of a predetermined feature value, and the like. For example, a region having a pixel value with a predetermined color luminance value equal to or higher than a predetermined threshold value is extracted as the lesion region.

Note that here, the processor 13 extracts the lesion region by image processing, but the data creator may set the lesion region in such a manner as to trace a boundary of the region of the lesion part using the input apparatus 17 such as a mouse, on the second image G2 displayed on the display apparatus 16.

The processor 13 performs alignment of the first image G1 and the second image G2 (S4). In S4, two or more feature points in each of the first image G1 and the second image G2 are extracted, and based on the two or more feature points that are extracted, a deviation amount of the first image G1 and the second image G2 is detected and adjusted. Note that positions of a blood vessel pattern in the first image G1 and a blood vessel pattern in the second image G2 or the like may be compared, and the deviation amount of the first image G1 and the second image G2 may be detected. A process in S4 configures an alignment unit configured to perform alignment of the first medical image and the second medical image.

Figure 4:
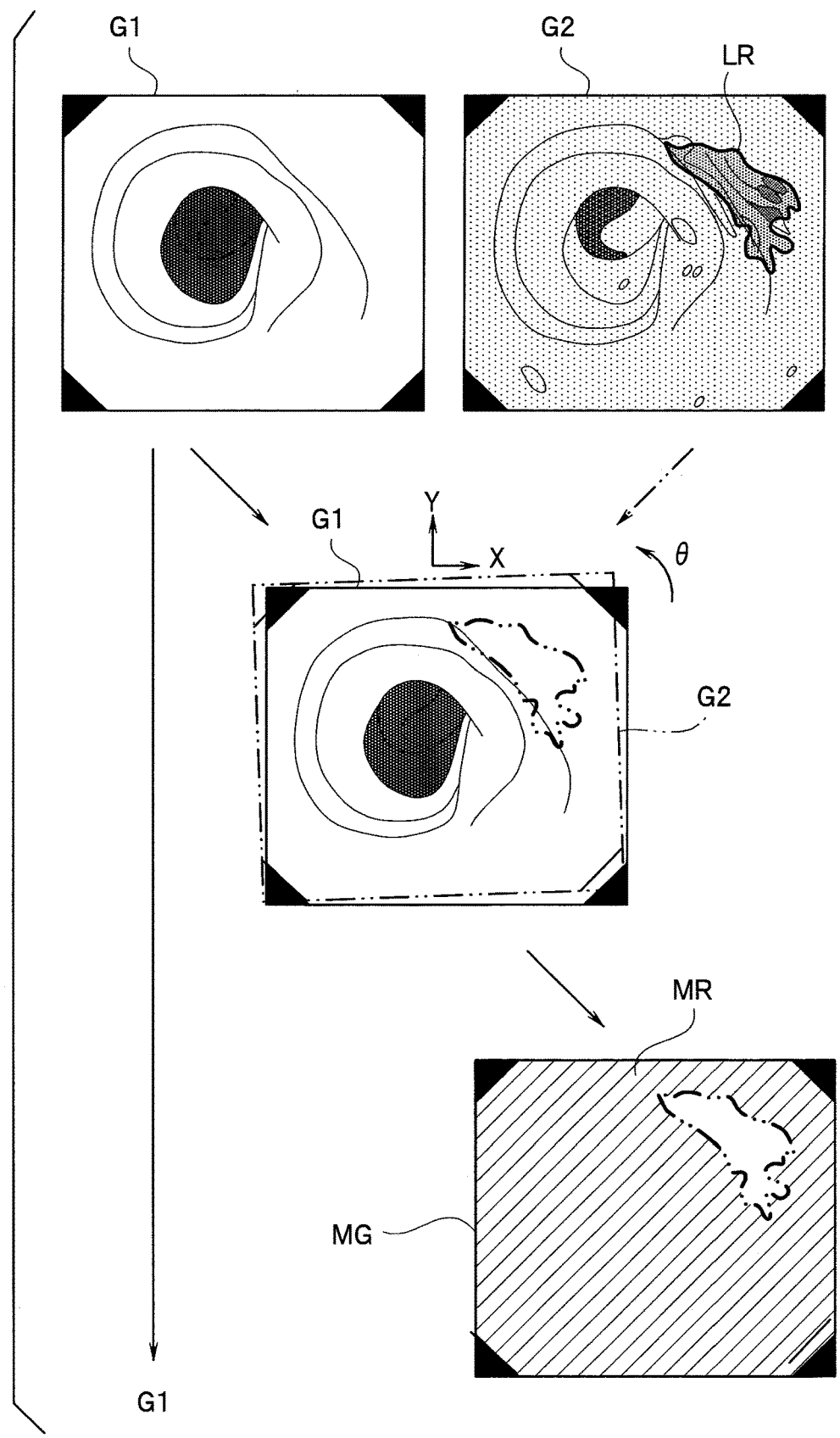
FIG. 4 is a view for explaining a creation process of training data according to the present embodiment.

FIG. 4 is a view for explaining a creation process of the training data. In S1 and S2, the first image G1 that is a white light image and the second image G2 that is a narrowband light image are selected by the data creator. The first image G1 is a white light image, and the lesion part is displayed to be difficult to recognize visually. On the other hand, the second image G2 is a narrowband light image using the aforementioned two narrowband lights, and a lesion region LR is recognizably displayed in the second image G2. Since the second image is acquired at a different timing from a timing at which the first image G1 is acquired, the first image G1 and the second image G2 are different in viewpoint position or the like even though the first image G1 and the second image G2 are the images obtained by photographing substantially the same spot in the subject.

Thus, in S4, the two or more feature points in each of the first image G1 and the second image G2 are detected, the deviation amount of the second image G2 with respect to the first image G1 is calculated from the positions of the two or more feature points, and alignment of the first image G1 and the second image G2 is performed based on the calculated deviation amount. In FIG. 4, not only does a center position of the second image G2 shown by a two-dot chain line deviate with respect to a center position of the first image G1 in an XY direction, but also the second image G2 is rotated by an angle $\theta$ around a line-of-site direction with respect to the first image G1. Accordingly, in S4, a positional displacement amount in the XY direction and a rotational angle $\theta$ around the line-of-site direction of the second image G2 with respect to the first image G1 are detected, and alignment of a subject image in the first image and a subject image in the second image is performed.

Note that the alignment may include an enlargement or reduction process of a size of the second image G2 to adjust a size of the subject. This is because a distance to the subject from a distal end of the insertion portion 4a at a time of the first image G1 being acquired may be different from a distance to the subject from the distal end of the insertion portion 4a at a time of the second image G2 being acquired.

In the example in FIG. 4, the positional displacement amount in the XY direction and the rotational angle $\theta$ around the line-of-site direction of the second image G2 with respect to the first image G1 are detected. In addition, an angle formed by a line-of-sight direction of the first image G1 and a line-of-sight direction of the second image G2 may be detected, and alignment may be performed with respect to the angle. In other words, when a plane orthogonal to the line-of-sight direction of the first image G1 and a plane orthogonal to the line-of-sight direction of the second image G2 are not parallel with each other, the second image G2 may be corrected to deform so that the plane orthogonal to the line-of-sight direction of the second image G2 becomes parallel with the plane orthogonal to the line-of-sight direction of the first image G1.

After S4, the processor 13 performs setting of a mask region MR (S5). The mask region MR is a region that masks a region other than the lesion region LR in the first image G1. Accordingly, in FIG. 4, a region other than a region (shown by the two-dot chain line) in the first image G1, of the lesion region LR in the aligned second image G2 is the mask region MR (region shown by oblique lines) in a mask image MG. In S5, the mask image MG defining the mask region MR is generated.

Note that the mask region MR is set here, but lesion region information indicating a region of the lesion region LR may be generated in S5. More specifically, information specifying a region (in other words, the lesion region LR) shown by the two-dot chain line in the first image G1 in FIG. 4 may be generated in S5.

Accordingly, a process in S5 configures a lesion region information creation unit configured to create lesion region information (mask region information or lesion region information) concerning the lesion part in the second medical image (narrowband light image). In S5, the lesion region information is created from the lesion region of the lesion part in the second medical image, the alignment of which is performed with respect to the first medical image.

After S5, the processor 13 creates the training data and stores the training data in a training data table TBL of the training data storage region 14d (S6). The training data created here includes image data of the first image G1 and mask region information MRI of the mask image MG. In other words, the training data configures medical image data for training in which the first image G1 is associated with the lesion region information.

Figure 5:
FIG. 5 is a diagram showing a configuration of a training data table according to the present embodiment.

FIG. 5 is a diagram showing a configuration of the training data table TBL. The training data table TBL stores a plurality of sets of data, each of which includes the image data of the first image G1 and the mask region information MRI indicating the lesion region in the first image G1. As shown in FIG. 5, for example, first image data "G100001" and mask region information "MRI00001" configure one set of data. The data of each set configures one piece of training data. Accordingly, a process in S6 configures a data creation unit configured to create the medical image data for training that associates the first medical image (white light image) with the lesion region information.

By the above processes from S1 to S6 being executed, one piece of training data is created. Accordingly, the data creator can easily create a lot of training data that are the medical image data for training by repeating the processes from S1 to S6.

The created training data are used as the medical image data for training of the lesion part detection model of the lesion part detection algorithm of the lesion part detection program LDP. As the training data increase, the lesion part detection model obtained by machine learning is updated, and enhancement in lesion part detection accuracy of the lesion part detection algorithm is expected. The lesion part detection program LDP using the updated lesion part detection model is transmitted to the CAD apparatus 3 as shown by a dotted line from the server 11 via the network 12, and the software program of the lesion part detection algorithm is updated. As a result, in the endoscope apparatus 2, detection result information in which lesion part detection accuracy is enhanced is displayed on the display apparatus 7 with the endoscope image.

Consequently, according to the aforementioned embodiment, the medical image data creation apparatus for training that can easily create the training data can be provided.

Note that in the aforementioned embodiment, the alignment process of the first image G1 and the second image (S4) is performed, but the alignment process may not be performed in the case of the first image G1 and the second image G2 that are obtained at a timing of switching the observation mode.

For example, directly after a white light image is acquired in the white light observation mode, the operation panel 6c may be operated to switch the observation mode to the narrowband light observation mode from the white light observation mode, and directly after the switching, a narrowband light image may be acquired. In such a case, a position and an orientation of the insertion portion 4a of the endoscope 4 may remain almost unchanged.

Alternatively, when a white light image (or a narrowband light image) directly before switching, and a narrowband light image (or a white light image) directly after switching are automatically acquired as the first image G1 and the second image G2 respectively according to the switching timing of the observation mode, the position and the orientation of the insertion portion 4a of the endoscope 4 at times of the first image G1 and the second image G2 being acquired remain almost unchanged.

Accordingly, when the training data is created from the first image G1 and the second image G2 that are acquired in this manner, the process in S4 in FIG. 3 can be omitted.

In addition, in the aforementioned embodiment, the endoscope apparatus 2 has the two observation modes that are the white light observation mode and the narrowband light observation mode, the first image is a white light image, and the second image is a narrowband light image of two narrowband lights with the center wavelengths of 415 nm and 540 nm. However, the second image may be a narrowband light image of wavelength bands with center wavelengths other than 415 nm and 540 nm, as long as a desired lesion can be detected with the wavelengths.

The endoscope apparatus 2 may have the white light observation mode, and an observation mode other than the narrowband light observation mode. The first image is a white light image, and the second image may be a fluorescence observation image.

Further, the first image is a white light image, and the second image may be a stained image of an observation site stained with a Lugol solution containing iodine or the like, or a colored image of an observation site on which indigo carmine or the like is sprayed.

Furthermore, the first image is a white light image, and the second image may be an image obtained by other modality (an X-ray image, an ultrasound image or the like), an image containing a region where biopsy is performed with forceps thereafter, or the like.

According to the aforementioned embodiment and respective modifications, the training data can also be promptly created even in cases where it is difficult or impossible for a lesion part to be recognized by anyone other than an expert doctor, for example. As a result, the medical image data creation apparatuses for training of the aforementioned embodiment and respective modifications contribute to prompt provision of a CAD apparatus capable of presenting highly accurate biopsy sites with a reduced oversight rate of lesion parts.

Note that a program executing the operations described above is entirely or partially recorded or stored in a portable medium such as a flexible disk or a CD-ROM, or a storage medium such as a hard disk, as a computer program product. The program is read by a computer, and all or some of the operations are executed. Alternatively, a whole or a part of the program can be distributed or provided via communication networks. A user can easily realize the medical image data creation apparatus for training of the present invention by downloading the program via a communication network and installing the program in a computer, or installing the program in the computer from a non-transitory recording medium.

The present invention is not limited to the aforementioned embodiment, and various modifications, alterations and the like are possible within the range without departing from the gist of the present invention.

What is claimed is:

1. A medical image data creation apparatus for training comprising:
    at least one processor comprising hardware, wherein the at least one processor is configured to:
        acquire a first medical image in a first observation mode;
        acquire a second medical image that is obtained by photographing a substantially same spot as in the first medical image in a second observation mode different from the first observation mode;
        perform alignment of the first medical image and the second medical image;
        create lesion region information concerning a lesion part in the second medical image, the alignment of which is performed; and
        create medical image data for training a model by machine learning, wherein the medical image data is a set of data of the first medical image and mask region information in which the lesion region information in the second medical image, the alignment of which is performed, is associated with the first medical image.

2. The medical image data creation apparatus for training according to claim 1,
    wherein the first medical image and the second medical image are still images selected respectively from moving images.

3. The medical image data creation apparatus for training according to claim 1,
    wherein the first observation mode is a white light observation mode, and
    wherein the second observation mode is a narrowband light observation mode.

4. The medical image data creation apparatus for training according to claim 1,
    wherein the at least one processor is configured to:
        detect an angle formed by a line-of-sight direction of the first medical image and a line-of-sight direction of the second medical image; and
        perform the alignment based on the angle.

5. The medical image data creation apparatus for training according to claim 1,
    wherein the at least one processor is configured to create the lesion region information in such a manner as to trace a boundary of a region of the lesion part in the second medical image, the alignment of which is performed.

6. A lesion detection system comprising:
    the medical image data creation apparatus according to claim 1,
    wherein the at least one processor is configured to:
        create the model trained by machine learning using the medical image data;
        receive an endoscope image received from an endoscope apparatus in real time; and
        perform detection of a lesion part in the endoscope image using the model.

7. A medical image data creation method for training comprising:
    acquiring a first medical image in a first observation mode;
    acquiring a second medical image that is obtained by photographing a substantially same spot as in the first medical image in a second observation mode different from the first observation mode;
    performing alignment of the first medical image and the second medical image;
    creating lesion region information concerning a lesion part in the second medical image, the alignment of which is performed; and
    creating medical image data for training a model by machine learning, wherein the medical image data is a set of data of the first medical image and mask region information in which the lesion region information in the second medical image, the alignment of which is performed, is associated with the first medical image.

8. The medical image data creation method for training according to claim 7,
    wherein the lesion region information is created in such a manner as to trace a boundary of a region of the lesion part in the second medical image, the alignment of which is performed.

9. A non-transitory computer-readable recording medium recording a program, the program causing a computer to at least execute:
    acquiring a first medical image in a first observation mode;
    acquiring a second medical image that is obtained by photographing a substantially same spot as in the first medical image in a second observation mode different from the first observation mode;
    performing alignment of the first medical image and the second medical image;
    creating lesion region information concerning a lesion part in the second medical image, the alignment of which is performed; and
    creating medical image data for training a model by machine learning, wherein the medical image data is a set of data of the first medical image and mask region information in which the lesion region information in the second medical image, the alignment of which is performed, is associated with the first medical image.

10. The non-transitory computer-readable recording medium according to claim 9,
    wherein the lesion region information is created in such a manner as to trace a boundary of a region of the lesion part in the second medical image, the alignment of which is performed.

* * * * *